(12) United States Patent
Street et al.

(10) Patent No.: US 8,618,091 B2
(45) Date of Patent: Dec. 31, 2013

(54) COMPOSITION AND METHOD FOR TREATMENT OF MRSA

(75) Inventors: Cale Street, Edmonds, WA (US); Nicolas Loebel, Woodinville, WA (US); Lisa Pedigo, Lake Forest Park, WA (US)

(73) Assignee: Ondine International Ltd., St. Michael (BB)

( * ) Notice: Subject to any disclaimer, the term of this patent is extended or adjusted under 35 U.S.C. 154(b) by 180 days.

(21) Appl. No.: 13/544,225

(22) Filed: Jul. 9, 2012

(65) Prior Publication Data

US 2012/0277660 A1    Nov. 1, 2012

Related U.S. Application Data

(62) Division of application No. 12/512,295, filed on Jul. 30, 2009, now Pat. No. 8,247,406.

(60) Provisional application No. 61/085,577, filed on Aug. 1, 2008, provisional application No. 61/186,068, filed on Jun. 11, 2009.

(51) Int. Cl.
*A61K 31/54* (2006.01)
*A61K 31/13* (2006.01)
*A61K 31/155* (2006.01)

(52) U.S. Cl.
USPC ............... 514/222.2; 514/224.8; 514/579; 514/632

(58) Field of Classification Search
USPC ............ 514/222.2, 224.8, 579, 632
See application file for complete search history.

(56) References Cited

U.S. PATENT DOCUMENTS

| | | | |
|---|---|---|---|
| 6,211,335 B1 | 4/2001 | Owen et al. | |
| 6,583,117 B2 | 6/2003 | Owen et al. | |
| 6,607,522 B1 | 8/2003 | Hamblin et al. | |
| 2002/0022660 A1* | 2/2002 | Jampani et al. | 514/635 |
| 2003/0180224 A1 | 9/2003 | Brown et al. | |
| 2004/0147508 A1 | 7/2004 | Brown et al. | |
| 2009/0093470 A1* | 4/2009 | Loebel et al. | 514/224.8 |
| 2010/0029779 A1 | 2/2010 | Street et al. | |

FOREIGN PATENT DOCUMENTS

| | | |
|---|---|---|
| WO | 02096896 A | 12/2002 |
| WO | 2006050058 A | 5/2006 |
| WO | 2008070023 A | 6/2008 |
| WO | 2009048868 A | 4/2009 |

OTHER PUBLICATIONS

Johnson et al. Efficacy of an alcohol/chlorhexidine hand hygiene program in a hospital with high rates of nosocomial methicillin-resistant *Staphylococcus aureus* (MRSA) infection. MJA 2005; 183: 509-514.*
International Search Report & Written Opinion dated Nov. 24, 2009—Appln. No. PCT/US2009/052059.
International Preliminary Report on Patentability—Appln. No, PCT/US2009/052059.
Johnson PDR et al. Efficacy of an alcohol/chlorhexidine hand hygiene program in a hospital with high rates of nosocomial methicillin-resistant Staphyloccoecus aureus (MRSA) infection. MJA 2005: 183: 509-514.

* cited by examiner

*Primary Examiner* — Renee Claytor
(74) *Attorney, Agent, or Firm* — The Dobrusin Law Firm, PC

(57) ABSTRACT

The present invention provides a photosensitizing composition for treatment of MRSA comprising a photosensitizer and chlorhexidine and a pharmaceutically acceptable carrier. The present invention also provides a method for reducing disease causing microbes comprising: applying the composition comprising a photosensitizer, chlorhexidine at a concentration of more than about 0.01% and less than about 2% v/v, and a pharmaceutically acceptable carrier to a treatment site; and applying light to the treatment site at a wavelength absorbed by the photosensitizer so as to reduce the microbes at the treatment site.

28 Claims, 2 Drawing Sheets

| I | II | III | IV |
|---|---|---|---|
| a | 0.01% | 0.001% | 2.2 |
| b | 0.01% | 0.01% | 3.0 |
| c | 0.01% | 0.125% | 5.7 |
| d | 0.01% | 0.25% | 7.3 |
| e | 0.01% | 0.5% | 7.1 |
| f | 0.01% |  | 3.1 |
| g |  | 0.001% | 0.0 |
| h |  | 0.01% | 1.9 |
| i |  | 0.125% | 1.7 |
| j |  | 0.25% | 0.4 |
| k |  | 0.5% | 2.7 |

FIG. 2 ated on Jul. 30, 2009, which claims
COMPOSITION AND METHOD FOR TREATMENT OF MRSA

CLAIM OF PRIORITY

This application is a divisional of U.S. patent application Ser. No. 12/512,295, filed on Jul. 30, 2009, which claims benefit of provisional application Ser. No. 61/085,577 filed on Aug. 1, 2008 and provisional application Ser. No. 61/186,068, filed Jun. 11, 2009, which are all titled: "COMPOSITION AND METHOD FOR TREATMENT OF MRSA" and are hereby entirely incorporated by reference for all purposes.

FIELD OF INVENTION

The present invention provides a photosensitizing composition and a photodynamic disinfection method using such composition for treatment of Methicillin-resistant *Staphylococcus aureus* ("MRSA") that enhance MRSA treatment efficacy while reducing irritation and sensitivity to the host tissues at the treatment site.

BACKGROUND OF THE INVENTION

MRSA, a spherical Gram-positive aerobe, accounts for up to 50% of nosocomial *S. aureus* infections, and represents a multi-billion dollar problem in critical care units, intensive care units and general hospitals worldwide. Because bacteria naturally adapt to antibiotics, more than 95% of patients with MRSA do not respond to first-line antibiotics. Certain MRSA strains are now even resistant to glycopeptide antibiotics like Vancomycin®, removing the last remaining effective antibiotic treatment for the disease. Due to the fact that MRSA is resistant to most antibiotics such as methicillin, oxacillin, penicillin and amoxicillin, there is a need to treat MRSA without the use of antibiotics.

Photodynamic disinfection is a desirable alterative treatment method as it has been demonstrated to be an effective non-antibiotic antimicrobial approach in vitro. One exemplary advantage of photodynamic disinfection as a MRSA treatment modality is that, due to this non-specific bactericidal mechanism, it is typically not subject to issues of resistance that can plague the use of antibiotics. As another exemplary advantage, it can be employed as a localized topical treatment that can be administered in areas such as the nasal cavities (e.g., nasal mucosa) where MRSA is mostly likely found in the human body.

Photodynamic disinfection fundamentally involves the use of light energy to activate one or more photosensitizers of a photosensitizing composition so that those photosensitizers can then either pass energy on directly to a substrate/target (type I reaction), or can interact with molecular oxygen to produce reactive oxygen species (type II reaction). These reactions mediate the non-specific reduction of MRSA and other microbial cells primarily via lipid peroxidation, membrane damage, and damage to intracellular components.

SUMMARY OF THE INVENTION

The present invention provides a photosensitizing composition for treatment of MRSA comprising a photosensitizer (e.g., phenothiazine) and chlorhexidine and a pharmaceutically acceptable carrier. As shown below, this composition when used for photodynamic disinfection of MRSA enhances MRSA treatment efficacy. Furthermore, in one embodiment of the present invention, the photosensitizing composition also reduces and/or eliminates irritation and sensitivity to host tissues at the treatment site.

The present invention also provides a method for treatment of MRSA comprising: applying the composition comprising a photosensitizer, chlorhexidine and a pharmaceutically acceptable carrier to a treatment site; and applying light to the treatment site at a wavelength absorbed by the photosensitizer so as to reduce MRSA at the treatment site.

The present invention further provides a method for reducing disease causing microbes comprising: applying a composition comprising a photosensitizer, chlorhexidine at a concentration of more than about 0.01% and less than about 2% v/v, and a pharmaceutically acceptable carrier to a treatment site containing disease causing microbes; and applying light to the treatment site at a wavelength absorbed by the photosensitizer so as to reduce the microbes at the treatment site.

BRIEF DESCRIPTION OF THE DRAWINGS

The features and inventive aspects of the present invention will become more apparent upon reading the following detailed description, claims, and drawings, of which the following is a brief description:

FIG. 2 is a table showing the data collected for the experiments described below in Example II.

DESCRIPTION OF THE PREFERRED EMBODIMENT

Figure 1:
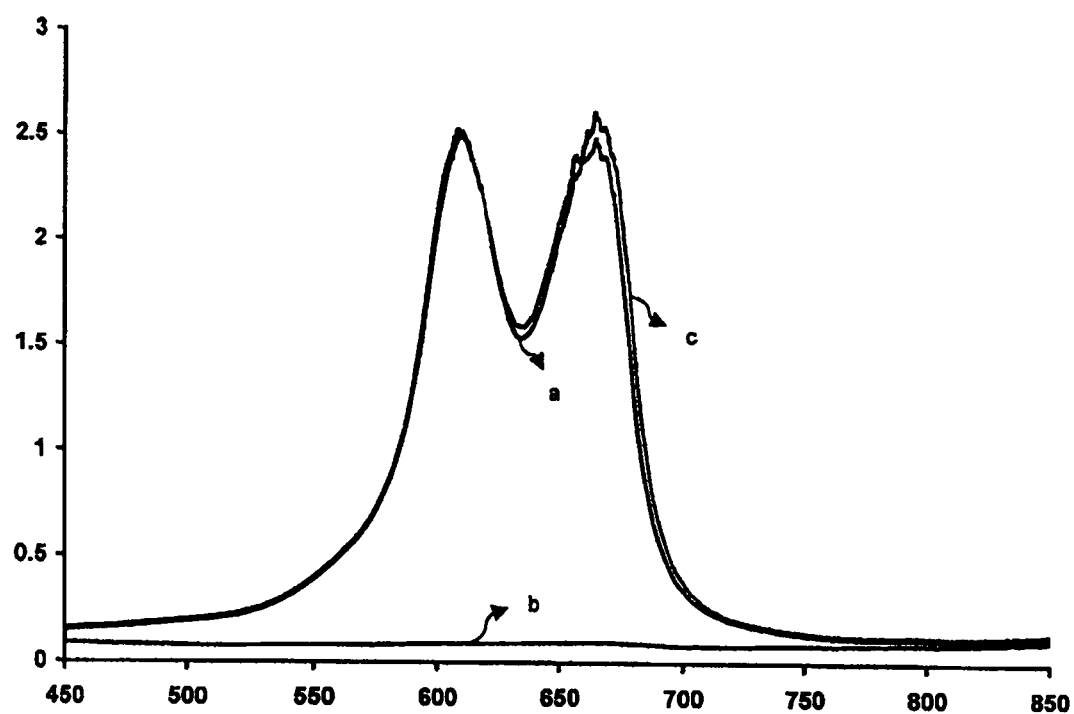
FIG. 1 is a graph showing the absorbance profile of three compositions described below in Example I.

In the present invention, chlorhexidine is combined with a photosensitizer to increase the effects of photodynamic disinfection to reduce, eliminate and/or kill (hereinafter collectively refer to as "reduce", "reducing", and/or "reduction") disease causing microbes such as MRSA or the like. The photosensitizing composition of the present invention includes a photosensitizer, chlorhexidine and a pharmaceutically acceptable carrier. As discussed below, the composition combines the powerful short-term antimicrobial effects of photodynamic disinfection with a more sustained chemical disinfection provided by chlorhexidine.

Chlorhexidine (e.g., chlorhexidine gluconate, chlorhexidine digluconate, chlorhexidine dihydrochloride, chlorhexidine diacetate or the like) is a broad spectrum antiseptic used for topical skin surface disinfection (e.g., surgical scrub or the like). For such application, chlorhexidine is commonly used in concentrations at ≥2 percentage of total volume ("% v/v"). See e.g., BactoShield® (2%, 4%), Betasept® (4%), ChloraPrep® (2%), Chlorostat®: (2%), Dial® Surgical Scrub (4%), Dyna-Hex (2%, 4%) Hibiclens®: (4%) and Operand® (2%). Irritation and sensitivity have been reported with such use of chlorhexidine containing products, especially in sensitive skin areas.

In one embodiment of the present invention, chlorhexidine is provided at a concentration that reduces and/or eliminates potential irritation and sensitivity to host tissues at the treatment area. This reduction and/or elimination of potential irritation and sensitivity is especially helpful when the host tissues at the treatment area are sensitive tissues such as the nasal mucosa. Exemplary suitable concentrations are about 1% v/v; about 0.5% v/v; about 0.25% v/v; about 0.125% v/v; between about 0.125% v/v and about 1% v/v; between about 0.125% v/v and about 0.8% v/v; between about 0.125% v/v and about 1.5% v/v; between about 0.25% v/v and about 0.5% v/v; between about 0.25% v/v and about 1% v/v; between about 0.25% v/v and about 1.5% v/v; a range that is less than about 1% v/v but more than about 0.1% v/v; a range that is less than about 0.8% v/v but more than about 0.1% v/v; a range that is less than about 2% v/v but more than about 0.1% v/v; and a range that is less than about 2% v/v but more than about 0.125%. The term "about" as used herein in this specification shall mean+/−20% of the stated value.

Examples of the photosensitizer include photosensitizers that effect both Type I and Type II photoreactions, where Type I reactions produce electron abstraction redox-type reactions upon the application of light and Type II reactions produce singlet oxygen (via molecular oxygen) upon the application of light. Suitable classes of compounds that may be used as the photosensitizer include tetrapyrroles or derivatives thereof such as porphyrins, chlorins, bacteriochlorins, phthalocyanines, naphthalocyanines, texaphyrins, verdins, purpurins or pheophorbides, phenothiazines, etc., such as those described in U.S. Pat. Nos. 6,211,335; 6,583,117; and 6,607,522 and U.S. Patent Publication No. 2003-0180224. Preferred phenothiazines include methylene blue, toluidine blue, and those discussed in U.S. Patent Publication No. 2004-0147508. Another preferred photosensitizer is indocyanine green. The present invention also contemplates the use of two or more photosensitizers, such as methylene blue and toluidine blue or the like. The photosensitizers mentioned above are examples and are not intended to limit the scope of the present invention in any way.

The photosensitizer may be present in the photosensitizing composition in any suitable amounts. Examples are between about 0.001 percentage of total weight (% wt) and about 10% wt, between about 0.005% wt and about 5% wt, between about 0.01% wt to about 1% wt, between about 0.01% wt to about 0.1% wt, and no more than about 1% wt. The percentage of total weight (% wt) can also be converted to percentage of total weight to volume (% w/v) or percentage of total volume to volume (% v/v). For the purpose of this specification, the concentration of photosensitizer can be expressed either in % wt, % w/v, or % v/v and such expression of concentration is intended to include its equivalences (e.g., if expressed in % wt, it is intended include the equivalent concentration measured in % w/v and % v/v).

As shown in Example II below, chlorhexidine significantly enhanced antimicrobial efficacy of photodynamic disinfection in reducing and/or eliminating microbial pathogens such as MRSA, even at low concentration levels such as between about 0.1% v/v and about 1% v/v. At chlorhexidine concentrations between 0.125% v/v and 0.5% v/v, the antibacterial activity of chlorhexidine and photodynamic disinfection combined is greater than would be expected considering just the additive effects of the two antibacterial methods on their own. This indicates an unexpected potentiation of antibacterial effect when low concentration of chlorhexidine and photodynamic disinfection are delivered simultaneously. This potentiation even occurs when chlorhexidine is used at a lower concentration than what is normally used for conventional topical skin disinfection. Thus, the lower concentration of chlorhexidine both reduces and/or eliminates irritation and sensitivity normally associated with chlorhexidine, and still acts to increase the antibacterial ability of the photodynamic reaction. This is especially important in the treatment of MRSA located in the nasal cavity due to the sensitivity of the nasal mucosa as a treatment site and the need to eradicate all MRSA pathogenic organisms to prevent recolonization.

The photosensitizing composition of the present invention further includes a pharmaceutically acceptable carrier. The pharmaceutically acceptable carrier is a diluent, adjuvant, excipient, or vehicle with which the other components (e.g., the photosensitizer and the chlorhexidine, etc.) of the composition are administered. The pharmaceutically acceptable carrier is preferably approved by a regulatory agency of the Federal or a state government, or listed in the U.S. Pharmacopeia or other generally recognized pharmacopeia for use in animals, and more particularly in humans. The pharmaceutically acceptable carriers are preferably sterile liquids. Examples of the pharmaceutically acceptable carriers include but are not limited to water, saline solution, dextrose solution, glycerol solution, phosphate buffered saline solution, etc.

It is further preferred that the pharmaceutically acceptable carrier, when combined with the photosensitizer and the chlorhexidine, allows the photosensitizing composition to have a viscosity low enough to flow into the treatment site while also having a viscosity high enough to maintain the composition within the treatment site. Further compositions that become liquid after application to the treatment site are contemplated such as those that melt or go into solution in the treatment site. Alternately, the composition may gel after application to the treatment site as a liquid; this would permit the composition to cover the treatment site effectively, while also maintaining the composition in the treatment site.

The present invention also provides a photodynamic disinfection method for treatment of MRSA comprising: applying the photosensitizing composition of the present invention described above to a treatment site; and applying light to the treatment site at a wavelength absorbed by the photosensitizing composition so as to reduce MRSA at the treatment site. The treatment site for the method of the present invention to treat MRSA would preferably be the nasal cavity (e.g., nasal mucosa) as it is generally known as an active site for MRSA. Photodynamic disinfection of the anterior nares of the nasal cavity reduces and/or eliminates MRSA.

It is preferred that prior to the application of light to the treatment site, the photosensitizing composition is placed into contact with the treatment site for at least about 1 second, more preferably for at least about 5 seconds, even more preferably for at least about 10 seconds, and most preferably from about 10 seconds to 30 seconds.

The light to be applied during the method of the present invention can be at any wavelength(s) that can be absorbed by the photosensitizer(s) contained in the photosensitizing composition. The wavelengths are generally between about 160 nm to 1600 nm, between about 400 nm to about 900 nm, and between about 500 nm to about 850 nm, although the wavelengths may vary depending upon the particular photosensitizing compound used and the light intensity. For example, if the photosensitizer is methylene blue, then the wavelength is preferably ranged from about 650 nm to 685 nm, more preferably from about 660 nm to about 680 nm, and most preferably at about 665 nm to about 675 nm.

The light produced may be a single wavelength or multiple wavelengths. The light may be produced by any suitable art-disclosed light emitting devices such as lasers, light emitting diodes ("LEDs"), incandescent sources, fluorescent sources, or the like. It is preferred that the light is produced either by a laser or LEDS.

Depending on the photosensitizer concentration and the power of the light emitting device(s), the application of light to the treatment site may only require a short period of time such as from about 15 seconds to less than about 5 minutes, preferably from about 15 seconds to about two minutes, more preferably for about 15 seconds to about 90 seconds, and most preferably for about 30 seconds to 60 seconds. The light energy provided during each cycle of application of light is preferred to range from about 1 J/cm$^2$ to about 25 J/cm$^2$, more preferably at about 5 J/cm$^2$ to about 20 J/cm$^2$, and most preferably at about 6 J/cm² to about 12 J/cm². Depending on the nature and extent of the MRSA located at the treatment site, the practitioner may apply multiple cycles of light applications (e.g., about 2 to about 10, about 3 to about 5, etc.) to the treatment site thereby resulting in a total accumulated light energy applied to treatment site that can be substantially higher than the light energy provided during each cycle. Again depending on the nature and extent of the microbes located at the treatment site, the entire method can be repeated multiple times (e.g., about 2 to about 10, about 3 to about 5, etc.) until the desired effects have been reached. It is preferred that the selections of photosensitizer concentration, wavelength, and/or total accumulated light energy applied to treatment site will allow the method of the present invention to reduce over about 90%, more preferably over 95%, and most preferably over 99% of the target MRSA at the treatment site. It is also preferred that the application of light to the treatment site does not cause physiological damage to the host tissues at and/or surround the treatment site.

The photosensitizing composition and the photodynamic disinfection method of the present invention discussed above can also be used to reduce other disease-related microbes such as virus, fungus, and bacteria. Some examples of such microbes include but are not limited to, *Staphylococcus aureus*, *Escherichia coli* ("*E. coli*"), *Enterococcus faecalis* ("*E. faecalis*"), *Pseudomonas aeruginosa*, *Aspergillus*, *Candida*, *Clostridium difficile*, *Staphylococcus epidermidis*, *Acinetobacter* sp., and pathogenic Gram negative organisms generally residing within the oral cavity (e.g., *Porphyromonas*, *Prevotella*, *Fusobacterium*, *Tannerella*, *Actinobacillus*, *Selenomonas*, *Eikenella*, *Campylobacter*, *Wolinella*, etc.).

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The following examples provided in accordance to the present invention are for illustrative purpose only and are not intended as being exhaustive or limiting of the invention.

Example I

Referring to FIG. 1, the characteristic absorbance profiles of the following three compositions are provided: (a) methylene blue at a concentration of 0.01% wt in pure water; (b) chlorhexidine gluconate at a concentration of 0.5% v/v in pure water; and (c) methylene blue at a concentration of 0.01% wt and chlorhexidine gluconate at a concentration of 0.5% v/v in pure water. The horizontal scale of FIG. 1 shows the absorbance per unit length (i.e., optical density). The vertical scale of FIG. 1 shows the wavelength in nm. The three lines (a, b, and c) in FIG. 1 represent the absorbance profiles of these three compositions. The characteristic absorbance profiles shown in FIG. 1 indicate that the addition of the 0.5% v/v chlorhexidine gluconate to the 0.01% wt methylene blue composition does not significantly alter the absorbance characteristics of the methylene blue in the visible wavelength range.

Example II

In vitro experiments were conducted by applying controls as described below and several different combinations of chlorhexidine digluconate and methylene blue compositions to planktonic cultures of MRSA (Methicillin-resistant *Staphylococcus aureus* ATCC® 33592™) at approximately $10^7$ CFU/ml. As shown in FIG. 2, these combinations consisted of the following active ingredients (a) methylene blue at a concentration of 0.01% wt and chlorhexidine gluconate at a concentration of 0.001% v/v; (b) methylene blue at a concentration of 0.01% wt and chlorhexidine gluconate at a concentration of 0.01% v/v; (c) methylene blue at a concentration of 0.01% wt and chlorhexidine gluconate at a concentration of 0.125% v/v; (d) methylene blue at a concentration of 0.01% wt and chlorhexidine gluconate at a concentration of 0.25% v/v; and (e) methylene blue at a concentration of 0.01% wt and chlorhexidine gluconate at a concentration of 0.5% v/v. Also shown in FIG. 2, the control formulations were consisted of (f) methylene blue at a concentration of 0.01% wt alone; (g) chlorhexidine gluconate at a concentration of 0.001% v/v alone; (h) chlorhexidine gluconate at a concentration of 0.125% v/v alone; (i) chlorhexidine gluconate at a concentration of 0.25% v/v alone; and (j) chlorhexidine gluconate at a concentration of 0.5% v/v alone. All of the above-mentioned planktonic MRSA cultures were irradiated by a non-thermal diode laser with 220 mW power output at a wavelength of 670 nm for 30 seconds (energy dose=10.3 Joules/cm²).

Thereafter, all of the planktonic MRSA cultures were examined and data regarding the amounts of planktonic MRSA reductions were collected. In FIG. 2, the composition number as discussed above is shown in column "I"; the concentration of methylene blue in each of the cultures is shown in column "II"; the concentration of chlorhexidine gluconate in each of the cultures is shown in column "III"; and the reduction in viability of planktonic MRSA (expressed as $\log_{10}$ reduction in viable colony count vs. non-treated control) for each of the cultures compared to a planktonic MRSA culture in purified water without any irradiation ("Control") is shown in column "IV". The rows in FIG. 2 show the result of each of the cultures discussed above. As shown in FIG. 2, the reduction in MRSA viability obtained using methylene blue alone at a concentration of 0.01% wt (see row "f") was 3.1 $\log_{10}$ compared to the Control, while the reductions of MRSA viability obtained after exposure to the chlorhexidine gluconate alone compositions (see rows "g", "h", "I", and "j") were between 0 to 2.7 $\log_{10}$ (depending on the chlorhexidine gluconate's concentration) compared to the Control. The data showed that the reduction in MRSA viability obtained after exposure to the methylene blue and chlorhexidine gluconate combined compositions in the presence of light corresponded to 100% eradication (>7.2 $\log_{10}$ reduction) when the chlorhexidine gluconate concentration was at either 0.25% v/v or 0.5% v.v. When the chlorhexidine gluconate concentration was at 0.125% v/v, the reduction in MRSA viability was >99.999% (5.7 $\log_{10}$ reduction). At chlorhexidine gluconate concentrations of 0.01% v/v or below, MRSA reductions were equivalent to that achieved using illuminated methylene blue alone, indicating that these concentrations of chlorhexidine were no longer contributing to antimicrobial efficacy.

The data provided in Example II shows that combining low concentration chlorhexidine gluconate (e.g., above 0.01% v/v) with photo-activated methylene blue results in a more powerful short-term antimicrobial effect of reducing MRSA than using photo-activated methylene blue alone. Several of the concentrations of chlorhexidine used in these studies were shown to have a measurable anti-microbial effect of reducing MRSA on its own; however it was significantly less than the photodynamic disinfection method of using the combination of low concentration of chlorhexidine and methylene blue.

Example III

In vitro experiments were conducted by applying either a control of purified water or the following Composition X to planktonic cultures of S. aureus (Staphylococcus aureus ATCC® 25923™) of approximately $10^7$ to $10^8$ CFU/ml. Composition X contained the active ingredients methylene blue at a concentration of about 0.01% v/v and chlorhexidine digluconate at a concentration of about 0.25% v/v in purified water. Cultures in purified water or Composition X were left in the dark or irradiated using a 670 nm non-thermal laser with a total energy dose of about 20.6 Joules/cm$^2$ (60 second exposure). After exposure, all samples were diluted and plated on solid media to observe subsequent growth. The reduction in viability of S. aureus in each experimental condition was compared to a planktonic S. aureus sample in purified water that received no irradiation ("Control").

The results showed significant antimicrobial efficacy against S. aureus after exposure to the irradiated Composition X. The irradiated Composition X achieved 5.4 $\log_{10}$ reduction in S. aureus viability compared to the Control. Exposure to the non-irradiated Composition X produced little reduction in viability of planktonic S. aureus, with about 0.7 $\log_{10}$ reduction in compared to the Control. This result indicates that, in the absence of light activation of methylene blue, the antimicrobial efficacy of 0.25% chlorhexidine digluconate after 60 second exposure was insignificant. Additionally, the samples in purified water that were irradiated showed no significant reduction in bacterial viability as compared to the Control indicating that the reduction effect was not due to thermal or light effects from the laser treatment alone. These results showed that the combination of a photosensitizer (e.g., a phenothiazine such as methylene blue) and chlorhexidine digluconate had a synergistic effect in providing significantly enhanced antimicrobial efficacy when used for photodynamic disinfection.

Example IV

In vitro experiments were conducted by exposing MRSA (Methicillin-resistant Staphylococcus aureus ATCC® 33592) at approximately $10^7$ to $10^8$ CFU/ml to a control of purified water or the following compositions. Composition A contained the active ingredients of methylene blue at a concentration of about 0.01% v/v and chlorhexidine digluconate at a concentration of about 0.25% v/v in purified water. Composition B contained the active ingredient of methylene blue at a concentration of about 0.01% wt in purified water. Composition C contained the active ingredient of chlorhexidine digluconate at a concentration of about 0.25% v/v in purified water.

MRSA bacterial inocula exposed to methylene blue (Compositions A and B) or purified water were irradiated using a 670 nm non-thermal laser with a total energy dose of 10.3 Joules/cm$^2$ (about 30 seconds of exposure). The inocula exposed to chlorhexidine digluconate alone (Composition C) received no irradiation but were left alone for 30 seconds before neutralization of the chlorhexidine using Dey-Engley broth. The neutralizing solution stops the antimicrobial activity of chlorhexidine thus allowing equivalent treatment and/or exposure times to test agent across all of the experimental samples.

After exposure, all samples were diluted and plated on solid media to observe subsequent growth. The reduction in viability of MRSA in each experimental condition was compared to a planktonic MRSA sample in purified water that received no irradiation ("Control").

The results showed that Composition A (methylene blue and chlorhexidine digluconate) was the most effective treatment for the eradication of MRSA. Exposure to this composition with irradiation produced a 7.3 $\log_{10}$ reduction in MRSA viability (100% eradication) compared to the Control. Irradiation in the presence of Composition B (methylene blue) produced a 4.8 $\log_{10}$ reduction in MRSA viability compared to the Control. Exposure to Composition C (chlorhexidine digluconate) produced negligible levels of eradication with only a 0.4 $\log_{10}$ reduction in MRSA viability compared to the Control. The samples in purified water that were irradiated showed no significant reduction in bacterial viability as compared to the Control indicating that the reduction effect was not due to thermal or light effects from the laser treatment alone. In summary, the antibacterial efficacy of the combined treatment of methylene blue and chlorhexidine digluconate with light irradiation was significantly better than that using chlorhexidine digluconate or irradiated methylene blue alone. This indicates a potentiation effect upon combination of these two agents that creates a more powerful antibacterial action than would be expected by the simple addition of the reduction effects seen with each separately.

Example V

In vitro experiments were conducted by exposing MRSA (Methicillin-resistant Staphylococcus aureus ATCC® 33592) at approximately $10^7$ to $10^8$ CFU/ml to either a control of purified water or the following compositions. Composition D contained the active ingredient of methylene blue at a concentration of about 0.01% w/v. Composition E contained the active ingredient of chlorhexidine digluconate at a concentration of about 0.125% v/v in purified water. Composition F contained the active ingredient of chlorhexidine digluconate at a concentration of about 0.25% v/v in purified water. Composition G contained the active ingredients of methylene blue at a concentration of about 0.01% w/v and chlorhexidine digluconate at a concentration of about 0.125% v/v in purified water. Composition H contained the active ingredients of methylene blue at a concentration of about 0.01% w/v and chlorhexidine digluconate at a concentration of about 0.25% v/v in purified water.

All methylene blue containing samples (Compositions D, G and H) were irradiated using a 670 nm non-thermal laser with a total energy dose of 10.3 Joules/cm$^2$ (about 30 seconds of exposure). The samples in purified water and chlorhexidine digluconate alone (Compositions E and F) received no irradiation but were left alone for 30 seconds before neutralization using Dey-Engley broth. This neutralizing solution stops the antimicrobial activity of chlorhexidine, thus allowing equivalent treatment and/or exposure times to test agent across all of the experimental samples.

After exposure, all samples were diluted and plated on solid media to observe subsequent growth. The reduction in viability of MRSA in each experimental condition was compared to a planktonic MRSA sample in purified water that received no irradiation ("Control")

The results showed that MRSA exposed to Composition D (methylene blue) with irradiation underwent a 4.8 $\log_{10}$ reduction in viability compared to the Control. Exposure to compositions E and F (chlorhexidine digluconate) produced no significant reductions in MRSA viability compared to the Control. Exposure to composition G (methylene blue and 0.125% chlorhexidine digluconate) with irradiation produced a 3.8 $\log_{10}$ reduction in MRSA viability compared to the Control. Exposure to composition H (methylene blue and 0.25% chlorhexidine digluconate) with irradiation produced the greatest antibacterial effect against MRSA, with a 7.3 $\log_{10}$ reduction in viability (100% eradication) compared to Control.

Based upon the data described above, the antimicrobial efficacy of the compositions containing both methylene blue and chlorhexidine digluconate was significantly better than that achieved with either agent alone. Furthermore, the reduction in MRSA viability for the combined treatment was greater than the combined efficacy of the two individual treatments, indicating a potentiation effect. This data suggests a true potentiation effect, as opposed to simply additive action of two different antibacterials, since the concentration of chlorhexidine digluconate tested alone had no effect on MRSA viability after a 30 second exposure.

As shown in Example I, the native optical absorbance profile of methylene blue is not altered in the presence of chlorhexidine digluconate. Therefore, it is unlikely that the two components complexed or significantly reacted to change the structure of one or the other. It is more likely that since chlorhexidine is known to act on the outer membrane of Gram-positive organisms, low concentrations that are not bactericidal alone permeabilize the bacterium to photosensitizer. This would allow increased membrane and intracellular aggregation of methylene blue molecules. The strong eradication of MRSA achieved by combining methylene blue with sub-lethal concentrations of chlorhexidine suggests that this may be a promising formulation for photodynamic disinfection of MRSA.

Example VI

A study was conducted to determine the efficacy of methylene blue, chlorhexidine digluconate and combinations thereof to eradicate biofilms of MRSA. Biofilms were grown in flat bottom 96-well culture plates by seeding each well with an inoculum of planktonic MRSA (Methicillin-resistant *Staphylococcus aureus* ATCC® 33592) at approximately $10^8$ CFU/ml and allowing growth for 48 hours with shaking at 35° C. to 37° C. After biofilms were established under this protocol, the liquid media was removed from test wells and the wells were rinsed twice using a phosphate buffered saline solution to remove all planktonic, non-biofilm associated organisms.

In vitro experiments were conducted by applying 200 μl of each of the following compositions to the biofilms for period of approximately 10 seconds. A control of phosphate buffered saline solution. Composition I containing the active ingredient of methylene blue at a concentration of about 0.01% v/v and chlorhexidine digluconate in a concentration of about 0.25% v/v in purified water. Composition J containing the active ingredient of methylene blue at a concentration of about 0.01% v/v in purified water. Composition K containing the active ingredient of chlorhexidine digluconate at a concentration of about 0.25% v/v in purified water. Composition L containing the active ingredient of chlorhexidine digluconate in a concentration of about 0.50% v/v in purified water. Composition M containing the active ingredient chlorhexidine digluconate in a concentration of about 0.125% v/v in purified water. Composition N containing the active ingredient of methylene blue at a concentration of about 0.01% v/v and chlorhexidine digluconate in a concentration of about 0.50% v/v in purified water. Composition O containing the active ingredient of methylene blue at a concentration of about 0.01% v/v and chlorhexidine digluconate in a concentration of about 0.125% v/v in purified water.

After 10 seconds, the compositions were all withdrawn from their respective the biofilm wells. The biofilm wells treated with methylene blue (Compositions I, J, N and O) were irradiated with a 670 nm non-thermal diode laser with a total energy dose of approximately 7 Joules/cm$^2$ (about 20 seconds of exposure). The biofilm wells exposed to the purified water composition or one of the chlorhexidine digluconate alone compositions (Compositions K, L and M) were left alone in the dark for 20 seconds without any irradiation. Immediately after the 20 seconds (with or without irradiation), a neutralizing solution of Dey-Engley broth was added to all of the biofilm wells in both test and control conditions. Once all of the biofilms had been exposed to the neutralizing solution, the well plate was transferred to an ultrasonicator on high setting for 30 minutes. Following ultrasonication, liquid samples from each well were plated on solid media to allow growth of surviving organisms. Plate colony counts were subsequently performed to determine MRSA eradication compared to the non-irradiated control of phosphate buffered saline solution ("Control").

The results showed that exposure to Composition J (methylene blue) with irradiation produced a 2.4 $\log_{10}$ reduction in MRSA viability compared to the Control. Exposure to composition L (0.50% v/v chlorhexidine digluconate) produced a 1.3 $\log_{10}$ reduction in MRSA viability compared to the Control. Exposure to composition K (0.25% v/v chlorhexidine digluconate) produced a 1.1 $\log_{10}$ reduction in MRSA viability compared to the Control. Exposure to composition M (0.125% v/v chlorhexidine digluconate) produced a 0.6 $\log_{10}$ reduction in MRSA viability compared to the Control. Thus, for the chlorhexidine digluconate only compositions (Compositions L, K and M), the data showed a decreasing antimicrobial efficacy against MRSA biofilms as the concentration of chlorhexidine digluconate decreased from 0.5% v/v to 0.125% v/v.

The results upon exposure to methylene blue and chlorhexidine digluconate with irradiation were as follows. Composition I (methylene blue and 0.25% v/v chlorhexidine digluconate) produced a 4.2 $\log_{10}$ reduction in MRSA viability compared to the Control. Composition M (methylene blue and 0.50% v/v chlorhexidine digluconate) produced a 4.5 $\log_{10}$ reduction in MRSA viability compared to the Control. Composition O (methylene blue and 0.125% v/v chlorhexidine digluconate) produced a 4.3 $\log_{10}$ reduction in MRSA viability compared to the Control. These results showed that the combined methylene blue with chlorhexidine digluconate compositions (Compositions I, N and O) produced superior antimicrobial efficacy compared to compositions containing methylene blue alone or chlorhexidine digluconate alone. Moreover, the reductions in viability achieved using the combination compositions were somewhat greater than the additive antibacterial effect of the individual components, thereby suggesting a potentiation effect. Furthermore, the antimicrobial efficacy for the combined methylene blue with chlorhexidine digluconate compositions (Compositions I, N and O) decreased only slightly as the chlorhexidine digluconate concentration decreased from 0.5% v/v to 0.125% v/v.

Example VII

This study was designed to assess the antibacterial efficacy of photodynamic disinfection, using various photosensitizer compositions, on human full thickness skin cultures colonized on the epithelial surface with high levels of MRSA.

Stock vials of MRSA (Methicillin-resistant *Staphylococcus aureus* ATCC® 33592) were kept frozen at −80° C. before use. Upon thawing, cultures were plated on tryptic soy agar (Hardy Diagnostics located in Santa Maria, Calif.) and grown at 37° C. until colonies were visible. These were subcultured to ensure growth phase and used to create inocula of ~$10^9$ CFU/ml for colonization of skin surfaces.

The human skin culture model used for this study was the EpiDerm FT™ Full Thickness Skin Model (MatTek™ Corporation located in Ashland, Mass.). This product consists of human-derived epidermal keratinocytes and human-derived dermal fibroblasts cultured at an air/media interface to form a stratified (epidermis and dermis), intact model of full thickness epithelialized human skin. These structures have been shown to exhibit differentiation markers, lipid profiles, and basement membrane structure characteristic of the in vivo situation and have been used extensively to study the effects of agents/treatments on human skin. Skin samples were received in cell culture inserts in 6-well plates from the manufacturer, and placed in culture at 37° C. (5% $CO_2$) for 24 hours after shipping to allow equilibration before use. A small volume (25 µl) of MRSA inocula, prepared as described above, was pipetted onto to the apical surface of the culture sample, taking care not to overflow to the sides of the insert, and incubated overnight at 37° C. (5% $CO_2$). Sterile cotton-tipped swabs were used to sample the inoculated tissue surfaces every 24 hours for 5 days post-inoculation in order to confirm stable colonization. Data showed that inoculating the epithelial surface of human skin cultures with $10^9$ CFU/ml of MRSA resulted in a stable colonization of ~$10^7$ CFU/ml (recoverable organisms after swab sampling) over a 5 day period.

Experiments were conducted by applying a control of purified water or one of the following compositions to the epithelial surface of MRSA colonized skin structures. Each of the samples of skin structures received a 50 µl aliquot of one of the following compositions: (i) a control of purified water ("Control"); (ii) Composition P contained the active ingredients of methylene blue at a concentration of about 0.01% v/v and chlorhexidine digluconate at a concentration of about 0.25% v/v in purified water; (iii) Composition Q contained the active ingredient of methylene blue at a concentration of about 0.01% wt in purified water; and (iv) Composition R contained the active ingredient of chlorhexidine digluconate at a concentration of about 0.25% v/v in purified water.

After application of either purified water, Composition P, Composition Q or Composition R, skin structures were placed directly under a 670 nm fiber-optically coupled laser system, which was terminated at an SMA-type connector and suspended using a laboratory stand/clamp. The tissue of each sample was placed at a distance of 7 cm from the terminating end of the fiber-optic source in order to produce a power density at the tissue surface equivalent to that of the surface of the MRSAid™ light diffuser tip manufactured by Ondine Biopharma Corp. located at Vancouver, B.C., Canada (~400 mW/$cm^2$). The samples were irradiated by a 670 nm nonthermal diode laser using this power density for about 120 seconds (total energy dose=about 48 Joules/$cm^2$). This method of irradiation was necessary since the MRSAid™ light diffuser tip itself could not be placed into the cell culture insert due to incompatibilities in size and shape.

After the 120 seconds, the samples received another 50 µl application of their respective composition (i.e., purified water, Composition P, Composition Q, or Composition R) and another round of irradiation for 120 seconds (total energy dose=about 48 Joules/$cm^2$) using the same process as described above. Thus, the samples received a total energy dose of 96 Joules/$cm^2$ from the two rounds of irradiation.

Immediately after the second round of irradiation, excess composition was removed from the treated surface of the samples. Sterile cotton-tipped swabs were used to sample the tissue surface, and these were neutralized to inhibit the action of chlorhexidine digluconate using a 0.45% v/v saline solution containing 3% tween-80 and 0.75% lecithin. Preliminary experiments confirmed that this solution effectively neutralized any chlorhexidine digluconate present on the swab before plating for viability assessment. Swabs were placed in liquid recovery media and samples were plated on solid media to observe subsequent growth. The reduction in viability of MRSA in each experimental condition was compared to a planktonic MRSA sample in purified water that received no irradiation ("Control")

Half of the treated skin structures were sampled immediately after treatment and the other half were incubated for 24 hours before sampling. Data from samples taken immediately post-treatment showed: (i) Exposure to composition Q (methylene blue) with irradiation resulted in a 0.2 $\log_{10}$ reduction in MRSA viability compared to the Control; (ii) Exposure to composition C (chlorhexidine digluconate) produced a 1.1 $\log_{10}$ reduction in MRSA viability compared to the Control; and (iii) Exposure to composition P (methylene blue and chlorhexidine digluconate) resulted in a 5.1 $\log_{10}$) reduction in MRSA viability compared to the Control. This immediate sampling data showed that the combination of methylene blue and chlorhexidine digluconate (Composition P) resulted in a significant and rapid reduction in MRSA viability when irradiated. In contrast, application of methylene blue alone (Composition Q) or light alone (irradiated control with purified water) did not result in significant reductions in viability compared to the Control immediately post-treatment.

Data from samples taken 24 hours post-treatment showed: (i) Exposure to composition Q (methylene blue) was equivalent to that of the Control immediately post-treatment; (ii) Exposure to composition R (chlorhexidine digluconate) produced a 4.3 $\log_{10}$ reduction in MRSA viability compared to the Control, which was significantly greater than that observed immediately post-treatment; and (iii) Exposure to composition P (methylene blue and chlorhexidine digluconate) resulted in a 5.9 $\log_{10}$ reduction in MRSA viability compared to the Control, which represented near total eradication of all colonized MRSA on that tissue surface.

These results indicate that Composition P, containing both methylene blue and chlorhexidine digluconate, was more effective at reducing colonization of MRSA on skin surfaces than the single ingredient compositions both immediately after treatment and at 24 hours post-treatment. The combination of a photosensitizer (e.g., a phenothiazine such as methylene blue) and chlorhexidine digluconate potentiated the reduction effect in comparison to the sum of that achieved with either agent alone.

Example VIII

A second study was conducted using the skin culture model described in Example VII to determine long term suppression of MRSA growth. Either a control of purified water or Composition S containing the active ingredients of methylene blue at a concentration of about 0.01% v/v and chlorhexidine digluconate at a concentration of about 0.25% v/v in purified water were applied to MRSA colonized skin samples and treated using the same application, irradiation, and sampling protocols and procedures described in EXAMPLE VII. Surface swab samples were taken at 24 hours, 48 hours and 120 hours post-treatment. Due to constraints on the number of samples available for testing, swab samples were not taken immediately post-treatment for this study.

At 24 hours post-treatment, exposure to composition S with irradiation resulted in a 3.6 $\log_{10}$ reduction in MRSA viability compared to the non-irradiated control (purified water). At 48 hours post-treatment and at 120 hours post-treatment, exposure to composition S resulted in total eradication of MRSA. In corresponding non-treated controls at those time points, bacterial viability remained in the $10^7$-$10^8$ CFU/ml range. This showed that the loss of bacterial viability in the treatment condition was not due to natural loss of colonization or decrease in tissue viability in the cultures.

Example IX

A third study was conducted using the skin culture model described in Example VII to determine long term suppression of MRSA growth. Either a control of purified water or one of the following compositions were applied to skin samples and treated using the same application, irradiation, and sampling protocols and procedures described in EXAMPLE VII. Composition T contained the active ingredient of methylene blue at a concentration of about 0.01% v/v and chlorhexidine digluconate in a concentration of about 0.25% v/v in purified water. Composition U contained the active ingredient of methylene blue at a concentration of about 0.01% v/v in purified water. Swab samples were taken (i) immediately after photodynamic disinfection treatment as described in EXAMPLE VII; (ii) at 24 hours post-treatment; and (iii) at 48 hours post-treatment.

The results showed that for samples taken immediately post-treatment, exposure to composition T (methylene blue and chlorhexidine digluconate) with irradiation produced a 1.1 $\log_{10}$ reduction in MRSA viability compared to its comparable non-irradiated control. For the 24 hours post-treatment samples, exposure to composition T with irradiation produced a 3.1 $\log_{10}$ reduction in MRSA viability compared to its comparable non-irradiated control. For the 48 hours post-treatment samples, exposure to composition T with irradiation produced a 3.5 $\log_{10}$ reduction in MRSA viability compared to its comparable non-irradiated control.

Furthermore, in the non-irradiated controls, the colonized MRSA counts increased over time with $\log_{10}$ counts of (i) 6.8 for the immediate post-treatment samples; (ii) 7.8 for the 24 hours post-treatment samples; and (iii) 8.4 for the 48 hours post-treatment samples.

Finally, the results showed that exposure to Composition U (methylene blue) with irradiation resulted in no significant reduction of MRSA viability compared to non-irradiated controls at any of the time points tested. These results showed that the combination of a methylene blue and chlorhexidine digluconate had a potentiation effect that provided significantly enhanced antimicrobial efficacy; suppressing MRSA growth over a 48 hour period.

What is claimed is:

1. A method of treating Methicillin-resistant *Staphylococcus aureus* ("MRSA") comprising:
   (a) applying a photosensitizing composition to treatment site comprising: a phenothiazine at a concentration from about 0.001% wt to about 1% wt; chlorhexidine at a concentration from about 0.125% v/v to about 0.5% v/v; and a pharmaceutically acceptable carrier; and
   (b) applying light to the treatment site at a wavelength absorbed by the photosensitizing composition so as to reduce the MRSA located at the treatment site.

2. The method of claim 1 wherein the phenothiazine is methylene blue.

3. The method of claim 1 wherein the phenothiazine is toluidine blue.

4. The method of claim 1 wherein chlorhexidine is chlorhexidine digluconate.

5. The method of claim 1 wherein concentration of the chlorhexidine is between about 0.25% v/v and about 0.5% v/v.

6. The composition of claim 1 wherein concentration of the phenothiazine is between about 0.01% wt to about 1% wt.

7. The method of claim 1 wherein the light applied to the treatment site in step (b) includes multiple wavelengths that are absorbed by the photosensitizing composition.

8. The method of claim 1 wherein the treatment site is the nasal cavity.

9. The method of claim 1 wherein the treatment site is anterior nasal nares.

10. A method for photodynamic disinfection of microbes comprising:
    (a) applying a photosensitizing composition to treatment site comprising: a phenothiazine at a concentration from about 0.001% wt to about 1% wt; chlorhexidine at a concentration from about 0.125% v/v to about 0.5% v/v; and a pharmaceutically acceptable carrier; and
    (b) applying light to the treatment site at a wavelength absorbed by the photosensitizing composition so as to reduce the microbes located at the treatment site.

11. The method of claim 10 wherein the phenothiazine is methylene blue.

12. The method of claim 10 wherein the phenothiazine is toluidine blue.

13. The method of claim 10 wherein chlorhexidine is chlorhexidine digluconate.

14. The method of claim 10 wherein concentration of the chlorhexidine is between about 0.25% v/v and about 0.5% v/v.

15. The method of claim 10 wherein concentration of the phenothiazine is between about 0.01% wt to about 0.1% wt.

16. The method of claim 10 wherein the light applied to the treatment site in step (b) includes multiple wavelengths that are absorbed by the photosensitizing composition.

17. The method of claim 10 wherein the treatment site is the nasal cavity.

18. The method of claim 10 wherein the microbes are selected from the group consisting of Methicillin-resistant *Staphylococcus aureus, Staphylococcus aureus, Escherichia coli, Enterococcus faecalis, Pseudomonas aeruginosa, Aspergillus, Candida, Clostridium difficile, Staphylococcus epidermidis, Acinetobacter* sp., *Porphyromonas, Prevotella, Fusobacterium, Tannerella, Actinobacillus, Selenomonas, Eikenella, Campylobacter, Wolinella* and a combination thereof.

19. A method for photodynamic disinfection of microbes comprising:
    (a) applying a photosensitizing composition to treatment site comprising: an effective amount of phenothiazine; an effective amount of chlorhexidine; and a pharmaceutically acceptable carrier; and
    (b) applying light to the treatment site at a wavelength absorbed by the photosensitizing composition so as to reduce the microbes located at the treatment; wherein the effective amount of phenothiazine and the effective amount of chlorhexidine produces a potentiation effect of antimicrobial efficacy during the photodynamic disinfection of microbes.

20. The method of claim 19 wherein the phenothiazine is methylene blue.

21. The method of claim 19 wherein the phenothiazine is toluidine blue.

22. The method of claim 19 wherein chlorhexidine is chlorhexidine digluconate.

23. The method of claim 19 wherein concentration of the chlorhexidine is between about 0.25% v/v and about 0.5% v/v.

24. The composition of claim 19 wherein concentration of the phenothiazine is between about 0.01% wt to about 1% wt.

25. The method of claim 19 wherein the light applied to the treatment site in step (b) includes multiple wavelengths that are absorbed by the photosensitizing composition.

26. The method of claim 19 wherein the microbes includes Methicillin resistant *Staphylococcus aureus*.

27. The method of claim 19 wherein the treatment site is the nasal cavity.

28. The method of claim 19 wherein the microbes are selected from the group consisting of Methicillin-resistant *Staphylococcus aureus, Staphylococcus aureus, Escherichia coli, Enterococcus faecalis, Pseudomonas aeruginosa, Aspergillus, Candida, Clostridium difficile, Staphylococcus epidermidis, Acinetobacter* sp., *Porphyromonas, Prevotella, Fusobacterium, Tannerella, Actinobacillus, Selenomonas, Eikenella, Campylobacter, Wolinella* and a combination thereof.

* * * * *